United States Patent
Li et al.

(10) Patent No.: US 11,650,300 B2
(45) Date of Patent: May 16, 2023

(54) ULTRASOUND SYSTEM AND METHOD FOR SUPPRESSING NOISE USING PER-CHANNEL WEIGHTING

(71) Applicant: KONINKLIJKE PHILIPS N.V., Eindhoven (NL)

(72) Inventors: Sibo Li, Cambridge, MA (US); Jean-Luc Francois-Marie Robert, Cambridge, MA (US); Francois Guy Gerard Marie Vignon, Andover, MA (US); Jun Seob Shin, Medford, MA (US); Seungsoo Kim, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 598 days.

(21) Appl. No.: 16/687,033

(22) Filed: Nov. 18, 2019

(65) Prior Publication Data
US 2020/0158844 A1 May 21, 2020

Related U.S. Application Data

(60) Provisional application No. 62/769,119, filed on Nov. 19, 2018.

(51) Int. Cl.
*G01S 7/52* (2006.01)
*A61B 8/08* (2006.01)
*A61B 8/00* (2006.01)

(52) U.S. Cl.
CPC ........ *G01S 7/52077* (2013.01); *A61B 8/5269* (2013.01); *A61B 8/54* (2013.01);
(Continued)

(58) Field of Classification Search
CPC ............... G01S 7/52077; G01S 7/5209; G01S 7/52095; G01S 7/5208; A61B 8/5269; A61B 8/54; A61B 8/4488; A61B 8/5207
See application file for complete search history.

(56) References Cited

U.S. PATENT DOCUMENTS

| | | | | |
|---|---|---|---|---|
| 2006/0173322 | A1* | 8/2006 | Cai | ........................ G01S 7/5209 600/437 |
| 2010/0286527 | A1* | 11/2010 | Cannon | .................... A61B 8/42 600/459 |

(Continued)

OTHER PUBLICATIONS

Dahl, et al., "Coherence Beamforming and its Applications to the Difficult-to-Image Patient", 2017 IEEE International Ultrasonics Symposium (IUS), Date of Conference Sep. 6-9, 2017, 10 pages.

(Continued)

*Primary Examiner* — Joseph M Santos Rodriguez
*Assistant Examiner* — Kaitlyn E Sebastian

(57) ABSTRACT

An ultrasound system according to the present disclosure may include a beamformer configured to perform per-channel weighting on the RF signals received at each channel in order to reduce noise clutter in the image. For this purpose, the beamformer may receive at one or more channels associated with an active aperture, sets of receive signals associated with respective transmit beams that at least partially overlap. The beamformer may alter the receive space, e.g., to align the sets of receive signals to a common location (e.g., between the transmit beams) and generate a coherence-based weighting value that may be indicative of blockage. The coherence-based weighting value may be applied on a per-channel basis to the receive signals. The beamformer may also communicate the coherence metric to the controller for altering the transmit space. In some such examples, the power output to one or more elements of the array may be adjusted based upon the
(Continued)

per-channel weighting value or determined blockage of the aperture.

20 Claims, 9 Drawing Sheets

(52) U.S. Cl.
CPC ........ *G01S 7/5209* (2013.01); *G01S 7/52095* (2013.01); *A61B 8/4488* (2013.01)

(56) References Cited

U.S. PATENT DOCUMENTS

| | | | | |
|---|---|---|---|---|
| 2012/0143058 | A1* | 6/2012 | Powers | G01S 15/8945 600/443 |
| 2015/0342567 | A1* | 12/2015 | Ustuner | A61B 8/5207 600/447 |
| 2016/0296202 | A1 | 10/2016 | Robert et al. | |
| 2018/0003811 | A1* | 1/2018 | Pellegretti | G01S 7/52077 |
| 2018/0203103 | A1* | 7/2018 | Pellegretti | G01S 7/52077 |

OTHER PUBLICATIONS

Wang, et al., "Analysis of signal coherence in ultrasound beamforming", 2013 IEEE International Ultrasonics Symposium (IUS), Date of Conference Jul. 21-25, 2013, pp. 809-812.

\* cited by examiner

ULTRASOUND SYSTEM AND METHOD FOR SUPPRESSING NOISE USING PER-CHANNEL WEIGHTING

RELATED APPLICATION

This application claims priority to and the benefit of Provisional Application Ser. No. 62/769,119, filed Nov. 19, 2018. These applications are hereby incorporated by reference herein.

TECHNICAL FIELD

The present disclosure pertains to ultrasound imaging systems and methods and particularly to such system and methods configured for reducing noise clutter, for example due to aperture blockage.

BACKGROUND

Blocked aperture is a significant cause of image degradation in ultrasound. The coherence method, whereby a coherence weighting mask is calculated then multiplied to the signal, has shown promise for attenuating the effects of clutter due to blocked apertures. However, existing coherence-based masking methods may not be ideal in certain scenarios, such as when the aperture is only partially blocked. Other techniques that may offer more effective and stable solutions for reducing noise due to blocked aperture may be desirable. Accordingly, designs and manufacturers of ultrasound imaging systems continue to seek improvements thereto.

SUMMARY

The present disclosure describes ultrasound imaging systems and method configured to apply per-channel weighting on the receive signals to reduce the noise clutter in the RF signals prior to beamsumming the RF signals and generating image data therefrom.

An ultrasound imaging system according to the present disclosure may include an array of transducer elements, a controller coupled to the array and configured to control the array to transmit a plurality of adjacent transmit beams toward a medium, the plurality of adjacent transmit beams including a first transmit beam and a second transmit beam at least partially overlapping the first transmit beam, and a beamformer coupled to the array via a plurality of channels and configured to receive, at a given channel, a first receive signal and a second receive signal responsive to the first transmit beam and the second transmit beam, respectively. The beamformer may be further configured to align the first receive signal to a location between the first and second transmit beams to produce a first aligned receive signal, align the second receive signal to the location between the first and second transmit beams to produce a second aligned receive signal, generate a weighting value for the given channel based on a correlation of the first and second aligned receive signals, apply the weighting value to at least one of the first and second aligned receive signals, to a receive signal aligned to a location other than the location between the first and second transmit beams, or a combination thereof, to produce a weighted per-channel signal for the given channel, and sum the weighted per-channel signals associated with multiple channels of the beamformer to produce a beamformed signal for ultrasonically imaging the medium.

In some embodiments, the beamformer may be configured to generate the weighting value based on correlating the first and second aligned receive signals at multiple depth locations in the medium. In some embodiments, the beamformer may be configured to compare the correlations of the aligned receive signals from multiple sets of aligned receive signals and wherein the weighting value is based on the comparison. For example, two sets of signals from two neighboring transmits may be aligned to one common location between the neighboring transmits and correlated and another set of signals from two other neighboring transmits may be aligned to a different common location between the two other neighboring transmits and correlated. The two correlations may be compared to determine the final weighting value to be applied to the channel. If both correlations are high, the signal from the channel may be heavily weighted (e.g., a high weighting value applied) and if both correlations are low, a low weighting value may be applied to the channel. If one of the correlation is high and the other low, a determination may be made that the channel is at the edge of a blockage (e.g., which may be perceived by the array at some steering angles but not others) and thus either a low weighting value for the most aggressive weighting, or some value between the set high and low weighting values may be used for less aggressive weighting. In some embodiments, the beamformer may compute a normalized cross-correlation value and use the normalized cross-coefficient value as the weighting value. In some examples, the cross-correlation value may be computed using a kernel spanning 3 to 5 wavelengths in fast time or 1 to 3 scan lines in beam space. In some embodiments, the beamformer may filter (e.g., bandpass filter) the aligned receive signals prior to computing the weighting value. In yet further examples, the amount of overlap of the plurality of at least partially overlapping transmit beams may be selected to achieve a beam density from 80 to 128 transmit events in a 90 degree span. Different beam densities may be used for sector scans or scans of other formats (such as linear, 2D and 3D convex, etc.) In some embodiments, the beamformer may be configured for multiline beamforming such as by simultaneously receiving multiple receive signals from the array via multiple channels from the plurality of channels of the active aperture and performing multiline receive beamforming in real-time using the multiple received signals. The clutter noise suppression according to the principles herein may be applied to any of the multiple channels receiving signals. In any of the examples herein, the coherence-based weighting on the per-channel data, e.g., as used to determine if one or more channels are blocked, may be further used to alter the transmit space. For example, controller of the ultrasound system may be communicatively coupled to the beamformer and configured to adjust the power output to one or more elements of the array based on the correlation of the aligned receive signals—e.g., if low correlation is computed and thus the element is deemed to be blocked, the power to the given element may be reduced or suppressed, which may increase the operational efficiency of the system by reducing power output to elements which in any case would produce low quality signals.

A method in accordance with the principles herein may include transmitting, from an array of transducer elements, a plurality of at least partially overlapping transmit beams including a first transmit beam and a second transmit beam, receiving, at a given channel associated with the active aperture of the array, a first receive signal responsive to the first transmit beam and a second receive signal responsive to the second transmit beam, aligning the first receive signal to a location between the first and second transmit beams to produce a first aligned receive signal, aligning the second receive signal to the location between the first and second transmit beams to produce a second aligned receive signal, generating a weighting value for the given channel based on a correlation of the first and second aligned receive signals, applying the weighting value to at least one of the first and second aligned receive signals, to a receive signal aligned to a location other than the location between the first and second transmit beams, or a combination thereof, to produce a weighted per-channel signal for the given channel, and summing the weighted per-channel signals associated with multiple channels of the active aperture to produce a beamformed signal for ultrasonically imaging the medium.

Any of the methods and/or steps thereof described herein, or functionality of one or more of the signal processing components described (such as the beamformer or other signal processing circuits) may be embodied in non-transitory computer-readable medium comprising executable instructions, which, when executed by at least one processor of a medical imaging system, cause the processor to perform the method, steps, or functionality embodied therein.

DETAILED DESCRIPTION

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

As noted above, blocked aperture is a significant cause of image degradation in ultrasound. The coherence method, whereby a coherence weighting mask is calculated then multiplied to the signal, has shown promise to attenuate the effects of clutter due to blocked apertures. Many coherence methods, however, are pixel based and coherently mask signals only where the whole aperture is noisy/corrupted. In such cases, coherence is computed based on the whole receive aperture. Such techniques may still be deficient where only part of the aperture is blocked. The inventors have discovered that a direct element weighting, which only attenuates the contributions of elements affected by the blockage, may be a more effective and stable solution than multiplying the image with a coherence mask based on the full aperture, providing the benefit of an image with reduced clutter contribution (especially noise clutter). Thus, in accordance with the principles of the present disclosure, a technique for suppressing clutter is presented which uses per-channel coherence weighting as opposed to traditional whole aperture coherence technique. In accordance with the examples herein, clutter (e.g., due to aperture blockage) is suppressed using per-channel weighting based on the local coherence of different transmit beams. In some embodiments, no additional transmits are required (i.e., the same transmit sequence as used for a particular mode of imaging (e.g., b-mode, Doppler, etc.) can be used) and only the receive space may be altered or augmented to obtain additional, in some cases, aligned on receive per-channel signals for purposes of correlation computations.

Figure 1:
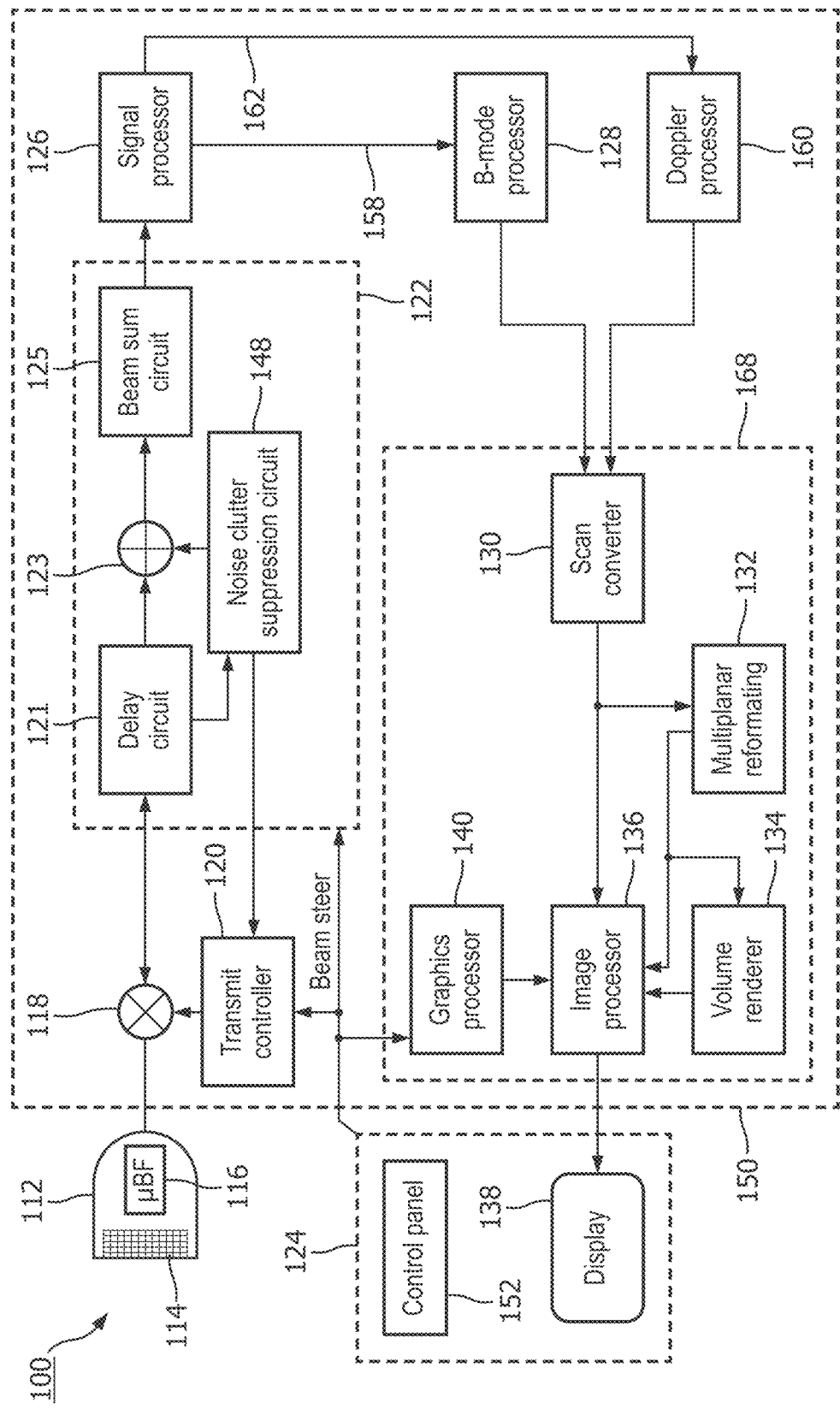
FIG. 1 is a block diagram of an ultrasound imaging system in accordance with the principles of the present disclosure.

FIG. 1 shows a block diagram of an example ultrasound imaging system, which includes a beamformer with enhanced noise clutter suppression according to the principles of the present disclosure. FIG. 1 shows array 114 and beamformer 122, which may include a delay circuit 121, a beam summing circuit 125, and a clutter suppression circuit 148. The system may also include additional data processing components configured to produce ultrasound images from the beamformed signals output by the beamformer 122. For example, the system may include signal processor 126, b-mode processor 128, and one or more display processors 168 (e.g., scan converter 130, multiplanar reformatter 132, volume renderer 134, image processor 136, etc.) for arranging the b-mode data for display. The components shown in FIG. 1 are exemplary only and variations, such as adding, omitting, combining or otherwise varying the arrangement of components shown in FIG. 1, are also envisioned. For example, while the processors 136, 134, 132, and 130 are shown, for illustration purposes, as separate components, in some implementations their functionality may be integrated into a signal processor 168 (which may be implemented using one or more processing units, e.g., a single processing cores or units or a plurality of processing units arranged for parallel processing).

The ultrasound imaging system 100 of FIG. 1 includes a transducer array 114, which in some examples may be provided in a probe 112. The transducer array 114, which may be interchangeably referred to as transducer or array, includes an array of transducer elements configured to transmit ultrasound beams toward a medium and detect echoes returning from the medium responsive to the ultrasound beams. A variety of transducer arrays may be used, e.g., linear arrays, convex arrays, or phased arrays. The transducer array 114, for example, can include a two dimensional array (as shown) of transducer elements capable of scanning in both elevation and azimuth dimensions for 2D and/or 3D imaging. The transducer array 114 may be coupled to a beamformer 122, which may be configured to perform transmit and receive beamforming. In some examples, the beamformer 122 may be configured to perform multiline receive beamforming and/or retrospective transmit beamforming (or beam focusing). The latter is performed retrospectively (i.e. after propagation of the transmit beam) on the received signals. The beamformer 122 may be configured for multiline beamformation and/or retrospective beam focusing in accordance with any of the examples in U.S. Pat. No. 6,695,783 (Henderson et al.), U.S. Pat. No. 8,137,272 (Cooley et al.) and U.S. Pat. No. 9,345,455 (Burcher et al.), which are incorporated herein by reference in their entirety for any purpose. The advancements achieved by multiline beamforming and retrospective beam focusing may be further enhanced by providing a beamformer in accordance with the examples herein which is capable of performing per-channel (or per-element) weighting on the time-aligned RF signals prior to summing the signals for image line generation.

In some embodiments, as in the illustrated example in FIG. 1, the transducer array 114 may be coupled to a microbeamformer 116 in the ultrasound probe 112. While not required, a microbeamformer 116 may be used to reduce the total number of channels between the array 114 and the ultrasound system base 150, which in exemplary systems contains the signal and image processing components. In some embodiments, one or more of the processors shown in FIG. 1 may instead be located in the probe 112. A microbeamformer 116, when provided, controls transmission and reception of signals by the transducer elements in the array 114. The microbeamformer beamforms signals from groups of elements in the array (also referred to as patches) and transmits these partially beamfored signals to a main beamformer in the base over a smaller number of channels then would otherwise be required. Regardless of whether a microbeamformer is included, the principles of the present disclosure apply equally and thus the term per-channel data as used herein may refer to either raw RF signals from individual elements of the array or the partially beamformed signals (for a reduced channel count) as received by the beamformer 122.

The array 114 may be coupled by a probe cable (although in other examples the two may be wirelessly coupled) to a transmit/receive (T/R) switch 118, which switches between transmission and reception and protects the beamformer 122 from high energy transmit signals. In some embodiments, for example in portable ultrasound systems, the T/R switch 118 and other elements of the system can be included in the ultrasound probe 112 rather than in the system base 150. The transmission of ultrasonic beams from the transducer array 114 under control of the beamformer 122 is directed by a controller 120, which may also be coupled to the T/R switch 118, e.g., for switching between transmit and receive events. The controller 120 may receive input from the user's operation of a user interface 124, such as for setting imaging parameters. The user interface 124 may include a display 138 for displaying image data acquired by the system 100 and one or more user-input devices, for controlling operations of the system 100, and which may be provided on a control panel 152 and/or on a touch sensitive display, which may be the same display that is used for displaying the images or an additional display. One of the functions that may be controlled by the controller 120 is the direction in which beams are steered. Beams may be steered straight ahead from (orthogonal to) the transducer array 114, or at different angles for a wider field of view.

The controller 120 may apply any currently known or later developed pulse-echo sequence (e.g., for B-mode or Doppler imaging) to acquire the raw echo signals, which are sent to the beamformer 122 for noise clutter suppression and beam formation. In accordance with the principles of the present disclosure, the beamformer 122 may be configured to provide noise clutter suppression based on per-channel evaluation of the coherence of signals from neighboring transmits. To that end, the beamformer 122 may alter or augment the receive space as compared to that associated with conventional imaging. That is, once the per-channel data has been received, the beamformer may generate additional, in some cases, aligned signals to those used for image formation based upon which per-channel weighting values are computed.

In the example in FIG. 1, the beamformer 122 includes a delay circuit 121 and a clutter suppression circuit 148. As further described herein (e.g., with reference also to FIGS. 2A-2C), the delay circuit 121 may be configured to apply a time or a phase delay to the individual per-channel signals to align sets of the per-channel signals from multiple transmit events to one or more location between the transmit beams. The sets of aligned per-channel signals are coupled to a noise clutter suppression circuit 148, which computes a coherence metric (e.g., a correlation value) of the sets of aligned per-channel signals. A high correlation (e.g., as may be determined using any suitable statistical measure) indicates that the signal at the particular channel is likely not affected by aperture blockage, while low correlation indicates that the per-channel signal is likely affected by aperture blockage. The circuit 148 generates a weighting value based upon the determined correlation, and the weighting value is applied (e.g., added at summation block 123) to the per-channel data before the per-channel data from the appropriate group of channels (e.g., associated with an active aperture) are coupled to the beam sum circuit 125 for appropriately summing and generation of a beamformed signal, which is then coupled to the signal processor 162 and downstream components for further processing and generation of image data (e.g., pixel data that may be used to produce and display B-mode images as an example).

In some examples, the beamformer 122 may be configured for multiline beam formation, which involves the generation of multiple scan lines from a single transmit, for example by insonifying a larger area encompassing several scanlines and then simultaneously receiving signals and forming beams at the multiple scanline locations. With appropriately designed apertures, multiline beamforming is capable of reconstructing multiple scan lines from a single transmit event. In some examples, the beamformer 122 may additionally or alternatively be configured to perform retrospective transmit beamforming on the received signals. For retrospective beamforming, the beamformer 122 adjusts (e.g., phase- or time-aligns) the signals to reduce out-of-phase or destructive interference and thus focus the transmit beam along a desired scanline. This adjustment is done by operating on the received signals, which are affected by the round-trip beam profile, the adjustment causing the round-trip signals to appear as if they experienced dynamic transmit focusing. The beamformed signal (e.g., A-line or scanline signal) output by the beamformer 122 is then coupled to a signal processor 126, which processes the signal in various ways, such as bandpass filtering, decimation, I and Q component separation, and harmonic signal separation, in order to generate image data for display. The signal processor 126 may also perform additional signal enhancement such as speckle reduction, signal compounding, and noise elimination.

The processed signals (e.g., separated signal components such as IQ components) may be coupled to one or more processors for producing an image of the selected imaging mode (e.g., B-mode, Colorflow Doppler 160, vector flow, shear wave elastography, etc.). For example, for B-mode imaging, the processed signals are coupled to a B-mode processor 128, which can employ envelope (or amplitude) detection for producing an image of bodily structures. The image data produced by the B-mode processor 128 may be coupled to a scan converter 130 and a multiplanar reformatter 132. The scan converter 130 arranges the image data (or pixel values) in the spatial relationship from which they were received in a desired image format. For instance, the scan converter 130 may arrange the echo signal into a two dimensional (2D) sector-shaped format, or a pyramidal or otherwise shaped three-dimensional (3D) format. The multiplanar reformatter 132 can convert echoes, which are received from points in a common plane in a volumetric region of the body into an ultrasonic image (e.g., a B-mode image) of that plane, as described in U.S. Pat. No. 6,443,896 (Detmer), which is incorporated herein by reference in its entirety for any purpose. The multiplanar reformatter 132 may thus reconstruct a 2D image (an MPR image) from a 3D (volumetric) dataset. The acquired image data may also be coupled to a volume renderer 134, which can convert the echo signals of a 3D dataset into a projected image of the 3D dataset as viewed from a given reference point (also referred to as volume rendering), e.g., as described in U.S. Pat. No. 6,530,885 (Entrekin et al.), which is incorporated herein by reference in its entirety for any purpose.

Images produced by the scan converter 130, multiplanar reformatter 132, and/or volume renderer 134 may be coupled to an image processor 136 for further enhancement, buffering, and temporary storage prior to display on the display unit 138. In some embodiments, the system 100 may further include a graphics processor 140, which can generate graphic overlays for display with the images. These graphic overlays can contain, e.g., standard identifying information such as patient name, date and time of the image, imaging parameters, or virtually any type of annotation or marking added to the images, automatically by the system or responsive to user inputs. For these purposes, the graphics processor may receive input from the user interface 124, such as a typed patient name or other annotations. As previously described, while the various image processing components are shown separately for the facility in describing their function, in some embodiments, one or more functions of one or more of the processors discussed herein may be combined in a single processor (the operations of which may be divided among multiple processor operating in parallel).

Figure 2A:
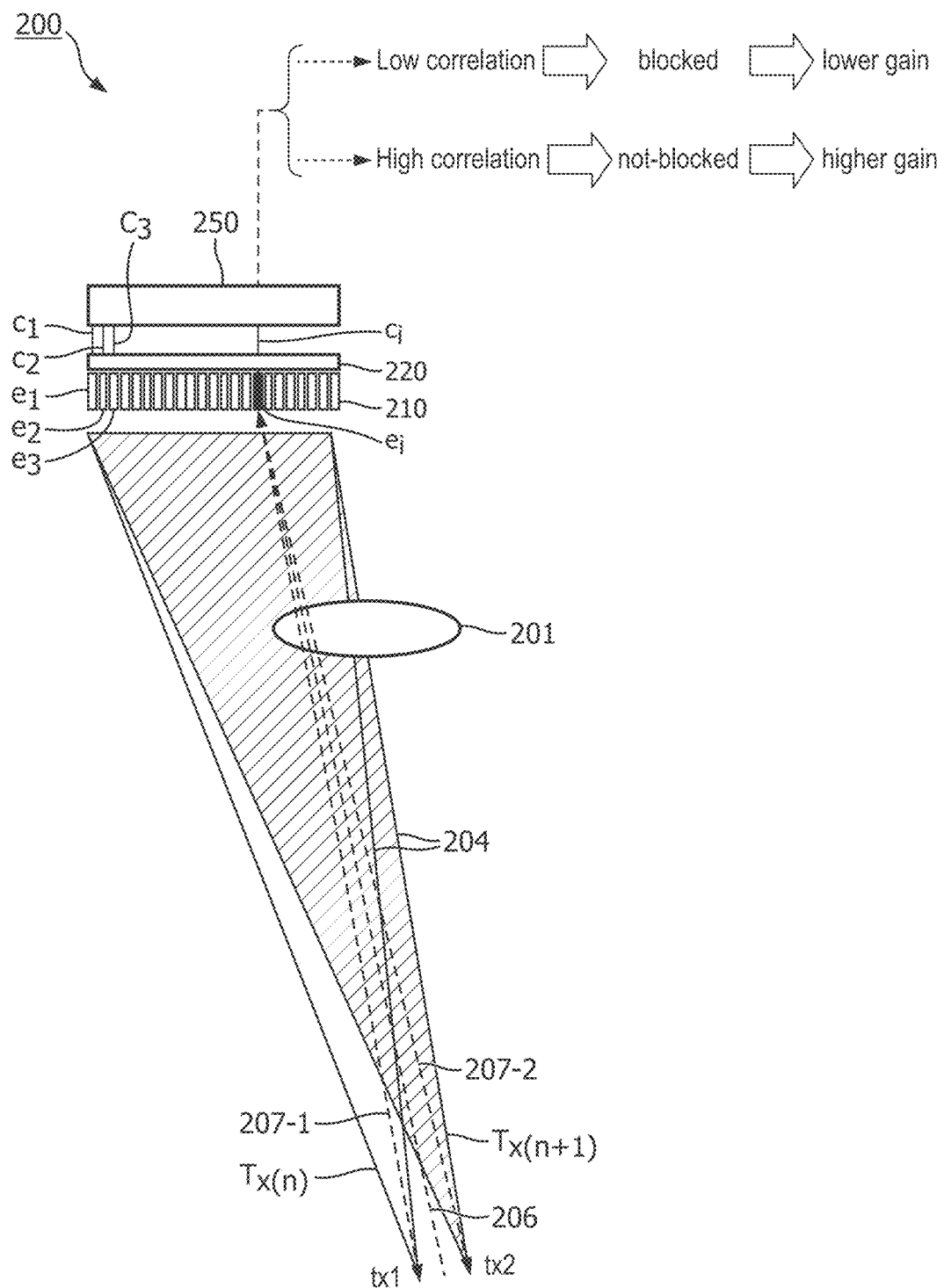
FIG. 2A is a block diagram of an array and associated components of a system illustrating principles of the present disclosure.
Figure 2B:
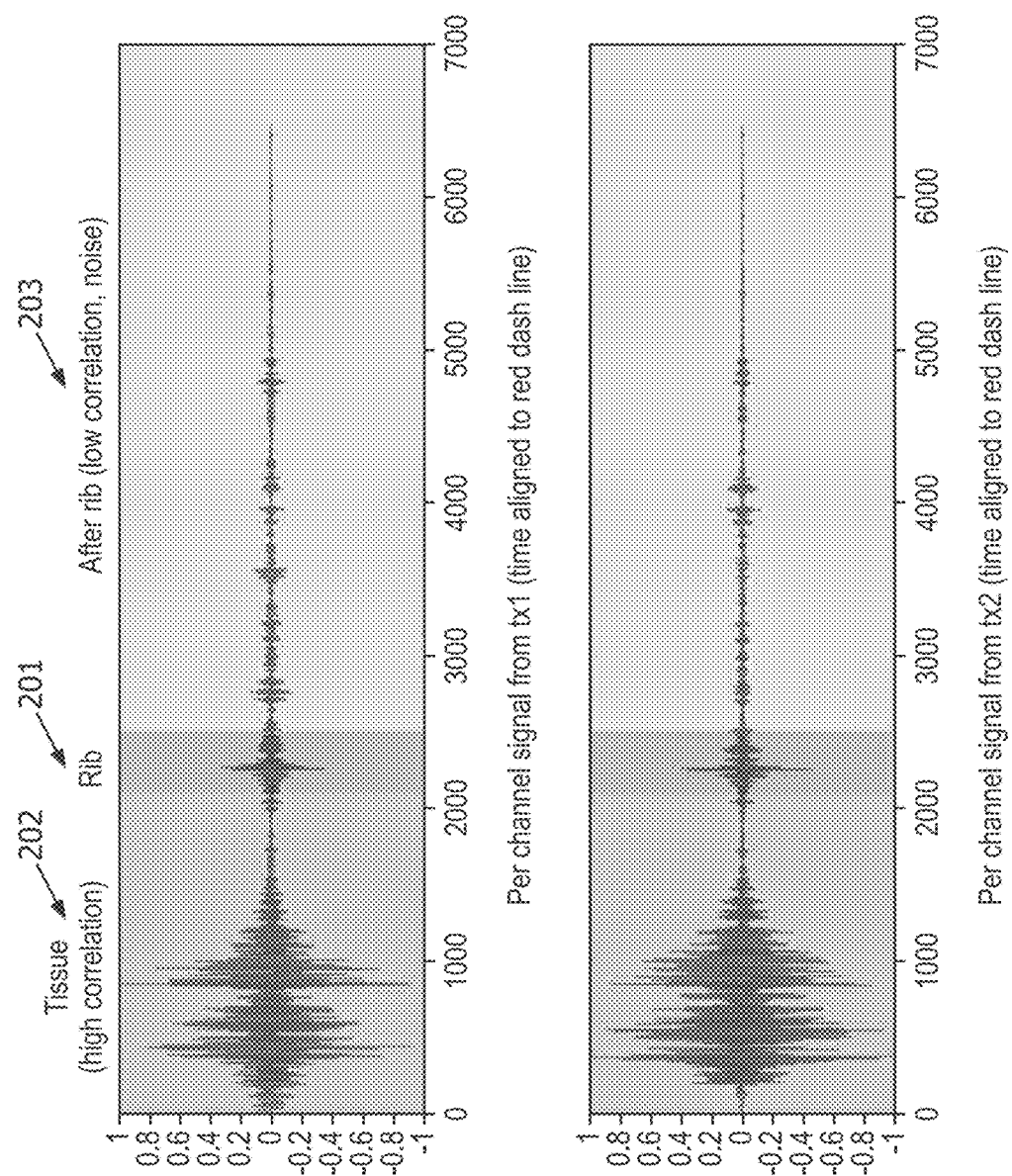
FIG. 2B illustrates an example of the aligned receive signal of neighboring transmits for noise clutter suppression in accordance with the principles of the present disclosure.
Figure 2C:
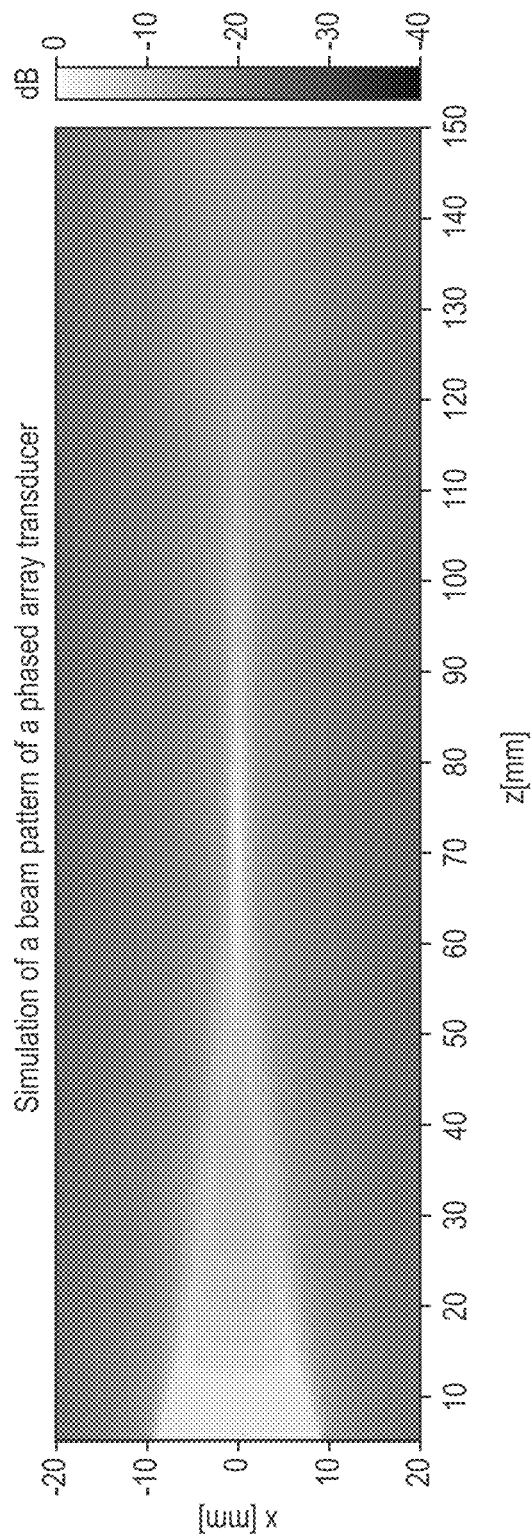
FIG. 2C illustrates a simulated transmit beam.

Referring now also to FIGS. 2A-2C, the operation of components of an ultrasound system in accordance with the principles of the present invention will be further described.

FIG. 2A shows an array 210 of elements connected to a beamformer 250 via a plurality of channels 220. The channels 220 couple the acoustic data (i.e. echo signals detected by elements of the array) to the beamformer 250. The acoustic data may initially be stored in acoustic data memory 220 (also referred to as channel memory 220) before it is coupled as channel data to the beamformer 250. As shown, the array 210 includes a plurality of elements e (e.g., $e_1$, $e_2$, $e_3$, and so on), each of which may be associated with a respective channel c (e.g., $c_1$, $c_2$, $c_3$, and so on). In some embodiments, e.g., where a microbeamformer is used between the array 210 and channel memory 220, the individual channels c may represent a partially beamformed signal from the echoes detected by a group of elements rather than from an individual element e. In either case, per-channel coherence weighting is applied to the signals received at the individual channels (e.g., $c_1$, $c_2$, $c_3$, and so on) prior to beamforming the receive signals into an image line.

FIG. 2A shows an illustration of two transmit-receive cycles during which two neighboring (or adjacent) transmit beams, which may overlap at least partially, are sent toward the medium (e.g., biological tissue of a subject) and signals are received and processed for image generation. As illustrated in FIG. 2A, a plurality of transmit beams 204 (e.g., Tx(n) and Tx(n+1)) are transmitted in sequence (e.g., one after the other) toward the medium using the same aperture (as shown in FIG. 2A) or using a different aperture for each transmit. The focal point and steering angle of each beam is controlled by appropriately activating the individual elements of the active aperture. For example, in a first transmit cycle tx1, elements of the array that are associated with the active aperture are activated in an appropriate manner (e.g., applying appropriate delays) to focus the first transmit beam (e.g., Tx(n)) to a desired location. In a second transmit cycle tx2, elements of the array that are associated with the active aperture, which may be the same as that of the first transmit beam, are activated in an appropriate manner (e.g., applying appropriate delays) to focus the second transmit beam (e.g., Tx(n+1)) to another desired location. The two focal points may be at the same axial depth in the tissue. The beams may have generally an hour-glass shape, as shown by the profiles or patterns of the beams Tx(n) and Tx(n+1) (shown only up to the focal point in FIG. 2A, and a further example of a simulated beam pattern shown also in 2C).

Also, while two transmits are shown for illustration, in other embodiments, the per-channel data from more than two transmits (e.g., three, four, or more), may be processed for computing a per-channel weighting value. Each transmit beam Tx(n) and Tx(n+1) is sent toward the medium using a respective transmit aperture, which is this example for illustration only, is shown to include the same group of adjacent elements (e) of the array. In other examples, the neighboring transmit beams may be generated using a different group of elements for each of the transmits. Any suitable shape may be used for the transmit beams (e.g., tightly focused beam focusing to a single transmit/receive line at the focal zone, or a wider beam spanning multiple lines at the focal zone). As illustrated in FIG. 2A, the active aperture may be at least partially blocked (e.g., by a hyperechoic structure 201, such as bone). Thus, the time-aligned per-channel signals associated with elements of the aperture that blocked (e.g., element $e_1$) may exhibit low correlation values indicating that those elements of the aperture are blocked and thus their contribution to the beamformer signals and ultimate to the image data should be reduced (e.g., by applying lower gain to those channels). For example, two sets of per-channel signals received at channel $c_i$ from two neighboring transmits (e.g., transmit events tx1 and tx2) time aligned to the same location in the receive space are shown in FIG. 2B. As can be perceived in the tissue region 202, the signal is similar, and thus the correlation value is high, while signals received from the region 203 behind the blockage 201, are not similar and thus the correlation value is low. As shown in FIG. 2B, the receive signals associated with the first and second transmits are recorded as a function of time, with the upper plot showing the per-channel receive signal (e.g., responsive to the first transmit) as a function of time, and the lower plot showing the per-channel receive signal (e.g., responsive to the second transmit) as a function of time. The correlation and noise suppression can be performed on the analog signal, or in some examples, the correlation and noise suppression functionality may be built into a digital beamformer. For the latter (i.e., if analyzing a discretized version of the received analog signal), the received signal is sampled at a sufficient sampling rate (e.g., at least a Nyquist sampling rate) to produce a digital or discretized receive signal. The correlation may be computed along the time direction, which relates to the axial/depth dimension, thus producing a correlation vector for each transmit-element pair.

During each transmit-receive cycle, pulse-echo signals are generated associated with the transmission and reception of ultrasound data. Each transmit-receive cycle includes a transmit event, during which a transmit beam (e.g., Tx(n) or Tx(n+1)) is sent into the medium along the transmit beam direction (or simply transmit direction) by generating appropriately timed pulses of ultrasound, and a receive event, during which echoes are detected following and responsive to the transmit event. In some examples, the transmit aperture (i.e., the elements active during transmission) may be the same as the receive aperture (i.e., the elements active during reception). In other examples, different apertures may be used on transmit and receive. In some examples, each of the transmit beams (e.g., Tx(n) and Tx(n+1)) may optionally be wide enough to each insonify a multitude of scanlines through the focal region and multiple image lines, such as by using multiline beamformation, may be generated responsive to each transmit event.

In accordance with the principles of the present disclosure, and as shown in FIG. 2A, the signals received at the individual channel are analyzed to generate coherence based per-channel weighting coefficients which are applied to the per-channel signals prior to the summation step. For example, for a given element ($e_i$) of the active aperture, the transmit path associated with each neighboring transmit is shown by lines 207-1 and 207-2. The signals received at the given element $e_i$ responsive to each of the two transmit events tx1 and tx2 are each aligned, by beamformer 250, to a same location between the two transmit paths (e.g., a location along the receive line 206). The receive line to which the per-channel signals at channel $c_i$ are aligned need not be strictly in the middle of the two transmit paths but may be any location therebetween. Each transmit/receive path corresponds to particular time delays to the signal transmitted/received from a given element. The alignment performed by beamformer 250 for purposes of weighting of the per-channel signals may but need not be the same as used to align the received per-channel signals for purposes of imaging (e.g., for aligning the echoes to a desired scan line). The location of the receive line between the two transmit beams to which the per-channel signals are aligned for purposes of weighting may be a location to also be used for generating image data, in which case the beamformer may select the appropriately time-aligned echo signals from the image data signal path and coupled those signals to the clutter suppression circuit for computing the coherence metric. In other examples, the receive line to align to for clutter suppression may be different from any scan line for imaging, in which case the beamformer may include additional delay circuit for the purposes of clutter suppression. For each point in the medium, the aligned signals can be represented by a matrix of size N by M, where N is the number of elements in the transmit aperture and M is the number of transmits which are being aligned to a common location, in this example M=2. Since each receive line in the medium is made up of multiple points, for each receive line in the medium, the aligned signals may be represented by a 3D matrix of size T by N by M, where T is the number of time samples used to represent the continuous signal as a discretized signal.

A coherence metric is then computed by beamformer 250 for each of the per-channel aligned signals, for example by computing the cross-correlation of the per-channel aligned receive signals from the two neighboring beams. Referring back to FIG. 2A, a low correlation computed for any given channel indicates blockage at that channel, which in some cases corresponds one to one with a corresponding element of the array, and thus indicates that lower gain should be applied to that channel, while a high correlation computed at a given channel indicates that that channel (e.g., element) is not blocked and thus higher gain can be applied to the signal at that location.

The general form for the zero-lag cross-correlation values of neighboring transmits is as follows: let $P_{Tx(n)}^{Rx(n,n+1)}(t, c)$ be the per-channel signal, where the subscript Tx(n) means the signal was acquired from the transmit event (n), and the superscript Rx(n,n+1) indicates the data was time aligned to the location in the middle of transmit (n) and (n+1), t and c denote the time samples and channel number. Note that in practice the per-channel data adopted for the correlation calculation can vary from adjacent transmit or every other adjacent transmit. By using a kernel k for the correlation, a depth-dependent vector (e.g., a zero-lag local cross-correlation vector) can be obtained, the expression for receive line (n, n+1) and channel c being:

$$W^{Rx(n,n+1)}(t, c) = \frac{\sum_{l=1}^{k}\left(P_{Tx(n)}^{Rx(n,n+1)}\left(t - \frac{k}{2} + l, c\right) \cdot P_{Tx(n+1)}^{Rx(n,n+1)}\left(t - \frac{k}{2} + l, c\right)\right)}{\sqrt{\sum_{l=1}^{k}\left(P_{Tx(n)}^{Rx(n,n+1)}\left(t - \frac{k}{2} + l, c\right)\right)^2 \cdot \sum_{l=1}^{k}\left(P_{Tx(n+1)}^{Rx(n,n+1)}\left(t - \frac{k}{2} + l, c\right)\right)^2}}, \quad \text{(eq. 1)}$$

where W is the weighting vector for per-channel signal. As previously noted, the correlation of aligned receive signals from adjacent overlapping transmits shows higher values in tissue. However, when there is noise (e.g., due to partial or full blockage of the aperture), the scattering path from different transmits can vary to some extent, and thus the correlation values would be lower. Also, in noisy areas (random noise), correlation values would also be low.

The per-channel coherence metric is then used to mask or weigh the signal received from each channel prior to beam summing the signals and generating the image lines. Each image line thus weighted is then used to produce an image of the medium, which in this example is presented in sector format (e.g., sector image 203), but in other examples may be scan converted to a different image format. Also, while a 2D image example has been described for simplicity, the technique of per-channel coherence weighting of the receive signals can be equally applied to three dimensional (volumetric) imaging. In addition, while the masking described in this example is applied on the receive signal, once a given channel and thus a corresponding one or more elements associated therewith, have been determined to be blocked (e.g., based on low correlation), the transmit even may also be tailored, such as by suppressing the power output of the blocked elements in the transmit space. In some such examples, the coherence metric and/or weighting coefficient computed by the beamformer may additionally be coupled to the transmit controller, which may reduce the power output to the blocked element(s) in a subsequent transmit.

Figure 3A:
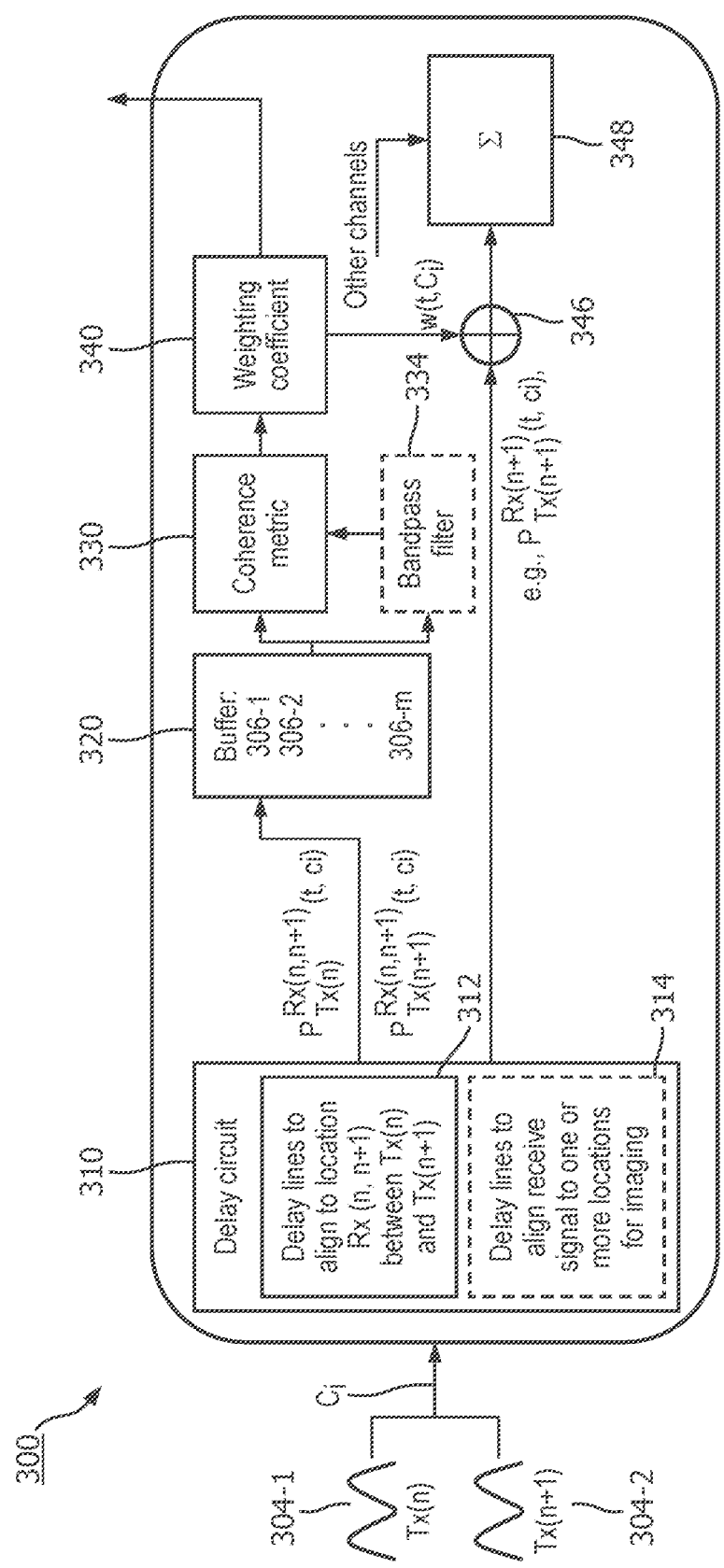
FIG. 3A shows, in block diagram form, a beamformer channel in accordance with the present disclosure.
Figure 3B:
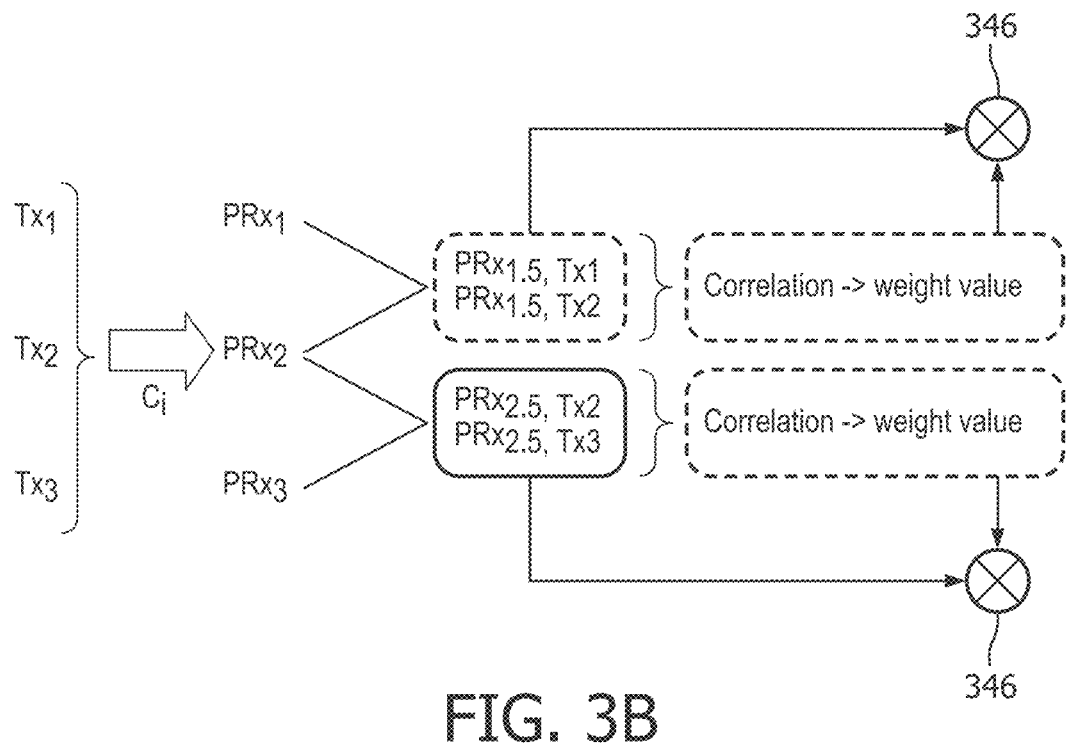
FIGS. 3B and 3C show examples of signal alignment and correlation performed by a beamformer in accordance with the present disclosure.
Figure 3C:
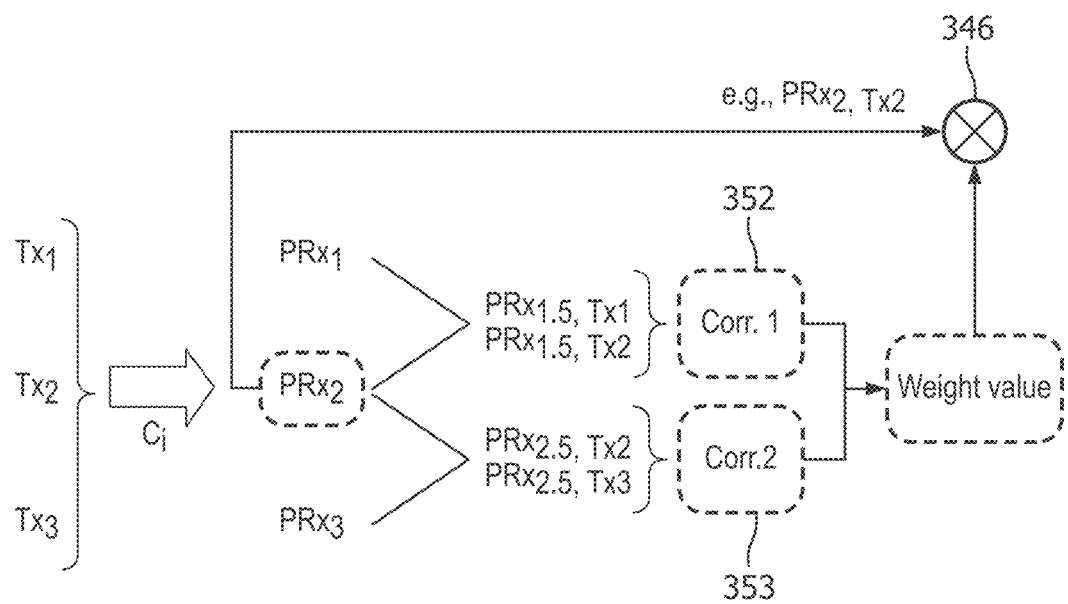

FIGS. 3A-3C show manipulations performed on the signal in the receive space. FIG. 3A shows a channel of a beamformer 300 and associated processing components in accordance with the principles of the present disclosure. As described, a beamformer according to the present disclosure receives from the array, via a plurality of channels, echo signals representative of the echoes detected at the individual elements of the aperture (or, as previously described, partially beamformed signals when a microbeamformer is used, e.g., for channel count reduction). In some embodiments, the noise clutter suppression circuitry of a beamformer according to the present disclosure may be equally applied to a microbeamformer.

During a given transmit-receive cycle, the beamformer receives, at any given channel $c_i$, echo signals 304-1 responsive to transmit beam Tx(n) and during a subsequent transmit-receive cycle, the beamformer receives, at channel $c_i$, echo signals 304-2 responsive to the neighboring transmit beam Tx(n+1). As described, the beams may be transmitted such that they overlap at least partially (e.g., as shown in FIG. 2A). Signal 304-1 is coupled to a delay circuit 310 which applies appropriate time or phase delays 312 to align the signal 304-1 to a location between the two transmits beams. Similarly, signal 304-2 received responsive to the neighboring transmit beam Tx(n+1) is also coupled to delay circuit 310 and aligned the same location to which signal 304-1 was aligned, as shown in block 314.

The delay circuit 310 may optionally include one or more additional delay lines 314 for aligning signals received at channel ci to any desired receive lines for purposes of beamformation for imaging. The delays appropriate to align the signal for clutter suppression may be the same or selected from those already used for imaging, in which case an additional delay circuit may not be needed from what is already employed by the beamformer for purposes of delay and sum beamforming. If an alternative method of beamforming is used (e.g., Fourier beamforming or other), an appropriately configured delay circuit may be provided solely for the purposes of noise clutter suppression within the beamformer. The per-channel aligned signals 306-1, 306-2, etc. output from the delay circuit 310 may be coupled to a buffer 320, where they may be temporarily stored until the multiple sets of aligned signals to be used for computing the coherence metric have acquired. In the case of weighting based on two transmits, a coherence metric is computed, at block 330, using the aligned signals 306-1 and 306-2 from the two transmits Tx(n) and Tx(n+1). For example, a normalized (zero-lag) cross-correlation between the aligned signals 306-1 and 306-2 from the two transmits Tx(n) and Tx(n+1) may be computed and assigned, at block 340, as the weighting coefficient $w(t,c_i)$. In other examples, a different coherence metric may be computed such as cross-correlation at higher lags, multiple lags, coherence factor, a generalized coherence factor, phase coherence, or others. The weighting coefficient w(t,c) may be optionally remapped, at block 340, by applying a gamma factor ($w^g$), exponential mapping ($g^w$), or some other suitable mapping function. Optionally, the aligned signals 306-1, 306-2, etc. may be bandpass filtered, at block 334, before computing the coherence metric. The weighting coefficient computed at block 340 may then be applied, (e.g., summed with the per-channel signal) at block 346 and passed to the beam summation block 348 for summing with per-channel weighted signals from other channels for generating the beamformed signal (also referred to as scan line or image line signal).

FIGS. 3B and 3C shows examples of signal alignment in the receive space for purposes of coherence based weighting and imaging. While the examples in FIGS. 3B and 3C are shown for three transmits, the principles described herein may equally apply to any number of transmits.

In the example with three transmits, for a given channel $c_i$, the receive signal responsive to each transmit $Tx_1$, $Tx_2$, and $Tx_3$ is indicated by $P^{Rx1}$, $P^{Rx2}$, and $P^{Rx3}$, respectively. That is, the signal received at channel $c_i$ responsive to transmit $Tx_1$ is $P^{Rx1}$, the signal received at channel $c_i$ responsive to transmit $Tx_2$ is $P^{Rx2}$, and the signal received at channel $c_i$ responsive to transmit $Tx_3$ is $P^{Rx3}$. IN some embodiments, the transmission and reception of raw echo signals $P^{Rxn}$ is unaffected by the current technique and conventional pulse-echo sequences can be employed to acquire the raw signals. A coherence based metric is computed, in this example, for each pair of receive signals from neighboring transmits, e.g., from the set of signals $P^{Rx1}$ and $P^{Rx2}$, and from the set of signals $P^{Rx2}$ and $P^{Rx3}$. In each instance, the receive signals in a given set are aligned to the same location, e.g., a location between the two transmits, indicated by $P^{Rx1.5}$ for the set of per-channel receive signals $P^{Rx1}$ and $P^{Rx2}$, and $P^{Rx2.5}$ for the set of signals $P^{Rx2}$ and $P^{Rx3}$. The output of the alignment process, which is perform by a delay circuit such as circuit 310, is a corresponding number of signals as the input signals. So in this example, the output is a pair of $P^{Rx1.5}$ signals that represent the time aligned first pair of signals, $P^{Rx1}$ and $P^{Rx2}$, aligned to a first common location between the two neighboring transmits $Tx_1$ and $Tx_2$. Similarly, a pair of $P^{Rx2.5}$ signals that represent the time aligned first pair of signals, $P^{Rx2}$ and $P^{Rx3}$, aligned to another common location, this time between the two neighboring transmits $Tx_2$ and $Tx_3$ are also produced by the delay circuit. A correlation is performed for each pair of time aligned signals (e.g., the two $P^{Rx1.5}$ signals, and the two $P^{Rx2.5}$ signals) and based upon the correlation, a corresponding weighting value (e.g., high weighting value for high correlation, and low weighting value for low correction) is generated. The weighting value is then applied to the receive signal aligned for image formation. In the example, in FIG. 3B, the same alignment is applied to the receive signals for image formation as used for the correlation. Thus, in the example in 3B, an image line is built on the "between" locations $Rx_{1.5}$, $Rx_{2.5}$, and for each transmit, an image line can be built by applying the weighting value to the corresponding aligned receive signal (e.g. $P^{Rx1.5}$, $P^{Rx2.5}$, etc.).

In the example in FIG. 3C, image lines are built on the original location and thus a different set of delay are applied for imaging and correlation. That is, for image line formation, the receive signal $P^{Rx1}$ is aligned to the location of transmit $Tx_1$, $P^{Rx2}$ is aligned to the location of transmit $Tx_2$ and so on. Weights can be applied to these aligned signals in a number of different manners. For example, once correlations 352 are computed for each set of neighboring receive signals, correlations from adjacent locations 353 may be compared for determining the weight to be applied to the receive signal aligned for imaging. For the receive signal responsive to $Tx_2$, single $P^{Rx2}$, the correlation between the sets of signals ($P^{Rx1}$, $P^{Rx2}$) and ($P^{Rx2}$, $P^{Rx3}$) are compared.

If both correlations (Corr. 1 and Corr. 2) are low, then line $Rx_2$ on this element is considered to be blocked, in which case, a low weight is applied the receive signal aligned to line $Rx_2$ (i.e., $P^{Rx2}$). If one of the correlations is high and the other low, the element $c_i$ is considered to be at the edge of a blockage. Weighting in this scenario can be aggressive, e.g., applying a low weight to the receive signal aligned to line $Rx_2$ (i.e., $P^{Rx2}$), less aggressive by applying a weight value somewhere between high and low. Furthermore, as described, the correlation analysis herein can be used to determine blocked elements and/or lines of the transducer aperture, and to adapt subsequent transmits to reduce the power to elements and/or lines determined to be blocked. That is, once it has been determine which elements or portion(s) of the aperture are blocked at certain sector angels, power output to those elements or portion(s) of the aperture can be suppressed in the transmit space, e.g., by providing this information to the transmit controller.

The functionality of the beamformer may be implemented in any suitable combination of software (e.g., in the form of executable instructions stored on computer readable medium, which program one or more processing units such as a CPU, GPU or the like, to perform the functions embodied in the executable instructions), hardware (e.g., in one or more application specific integrated circuits (ASICs), or a combination thereof. For example, a beamformer according to the present disclosure may include an analog beamformer, a digital beamformer, or a combination thereof. Similarly, other components of ultrasound systems according to the present disclosure (e.g., the signal and any other processor of the system) may be implemented in any suitable combination of hardware, software, or combinations therefor.

Figure 4:
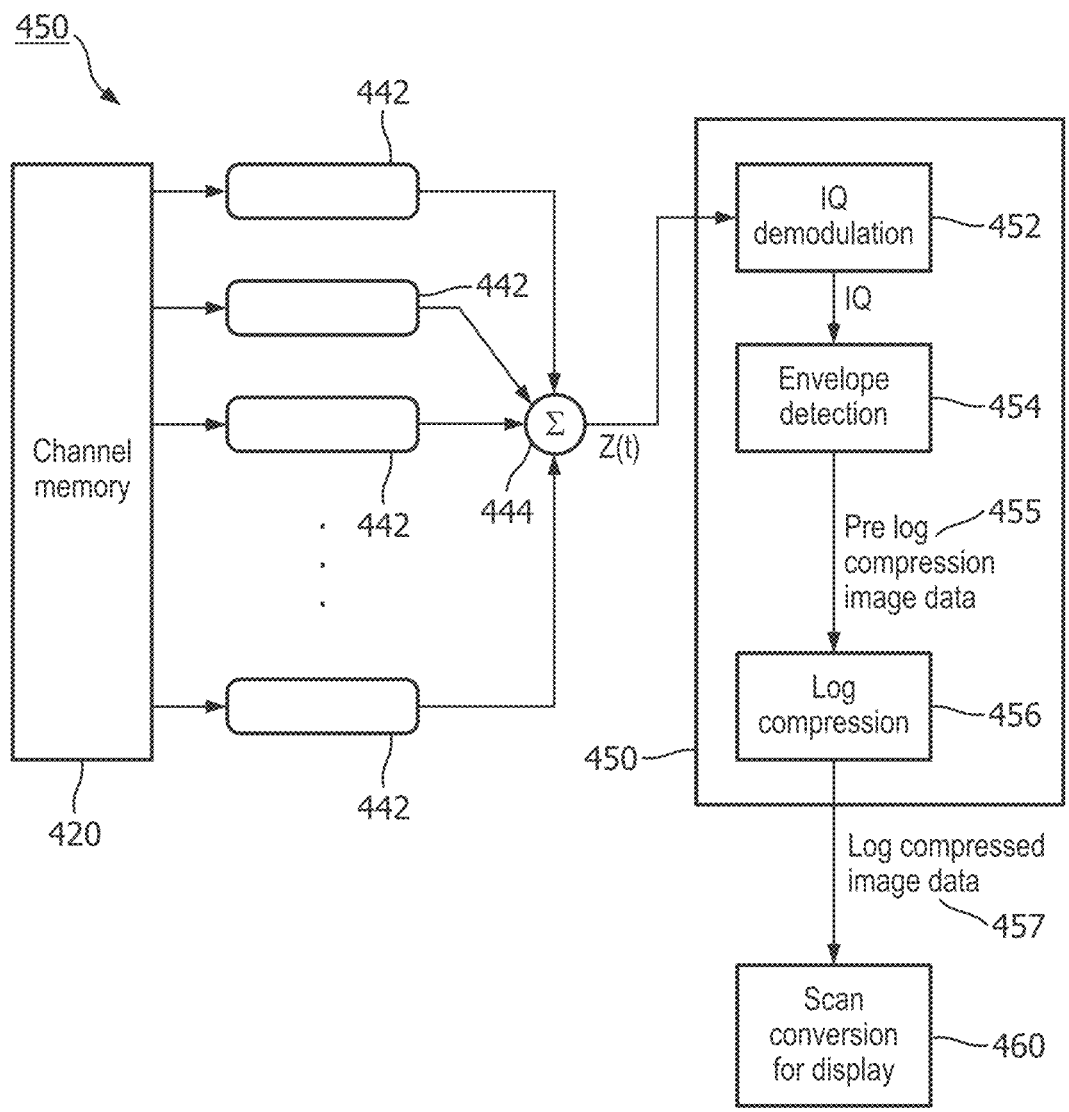
FIG. 4 shows, in block diagram form, beamformer channels and signal processing components of a system in accordance with the present disclosure.

FIG. 4 shows a block diagram of beam formation and signal processing components of a system in accordance with the principles of the present invention. The beamformer 450 in FIG. 4 receives per-channel data from channel memory 420 at each beamformer channel 442 which is associated with processing steps described above with reference to FIGS. 3A-3C, e.g. for time- or phase-alignment and weighting. The output of each block 442 is a weighted aligned signal, which is then beam summed at the summation block 444 to produce a beamformed signal z(t). The beamformed signal is coupled to a signal processor 450 for further processing. For example, signal processor 450 may perform demodulation at block 452 (e.g., to separate the signal z(t) into I,Q components) and envelope detection at block 454 to generate image data (e.g., echo intensity data prior to log compression). The pre log-compressed image data 455 may be coupled to log compression block 456 and the log compressed image data 457 may then be provided to further downstream image data processing components, such as to a scan converter 460 for appropriately arranging the image data for display. As will be appreciated, the final image produced by the ultrasound system would exhibit noise reduction in view of the augmentation (i.e. weighting) of the per-channel data at the beamforming stage.

Experimental Example

Figure 5:
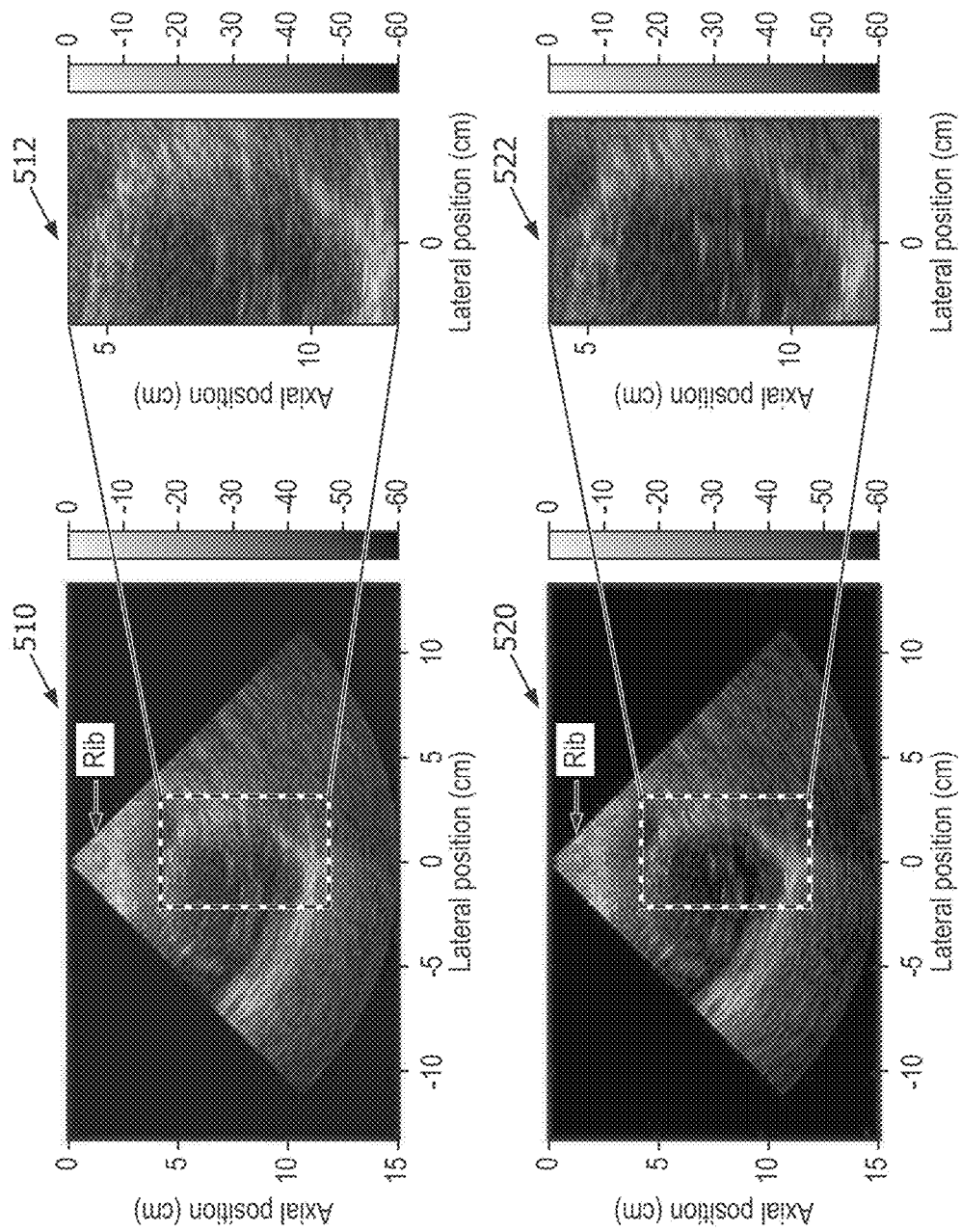
FIG. 5 shows ultrasound images without and with enhancement in accordance with the present disclosure.

FIG. 5 shows example images illustrating noise clutter reduction that may be obtained using the principles of the present disclosure. Image 510 and 520 show cardiac image datasets obtained from the same raw data in the first instance without noise clutter suppression and in the second instance with noise clutter suppression. The image data for generating images 510 and 520 was acquired with an 80-element S5-1 probe manufactured by PHILIPS. The image data was obtained using a beam density of 128 transmits in 90-degree span. The image 510 was formed with conventional delay-and-sum beamforming, while the image 520 was obtained in accordance with the principles of the present disclosure, specifically in this example using a weighting mapping function of $100^W$. As can be perceived, e.g., by observing the respective enlarged portions 512 and 522 of images 510, 520 respectively, the clutter from the rib shown at the top of each image is better suppressed in image 520, resulting in better resolution image where the tissue boundary is more clearly visualized, than in the image 510 generated using conventional delay-and-sum beamforming.

As will be appreciated, embodiments according to the present disclosure may vary depending on the beam density in transmit space, the parameter w that weights the per-channel signal, as well as other factors. Suitable beam density, in examples, may be anywhere from 80 to 128 transmit events in a 90 degree span. The weighting coefficient w weights the noise and thus controls the aggressiveness of the weighting. A normalized weighting coefficient (e.g., computed by remapping the correlation values to a min-max range of 0-1) has shown good results. A kernel size for the cross-correlation which spans 3 to 5 wavelength in fast time or 1 to 3 A-lines in beam space has also shows good results.

Figure 6:
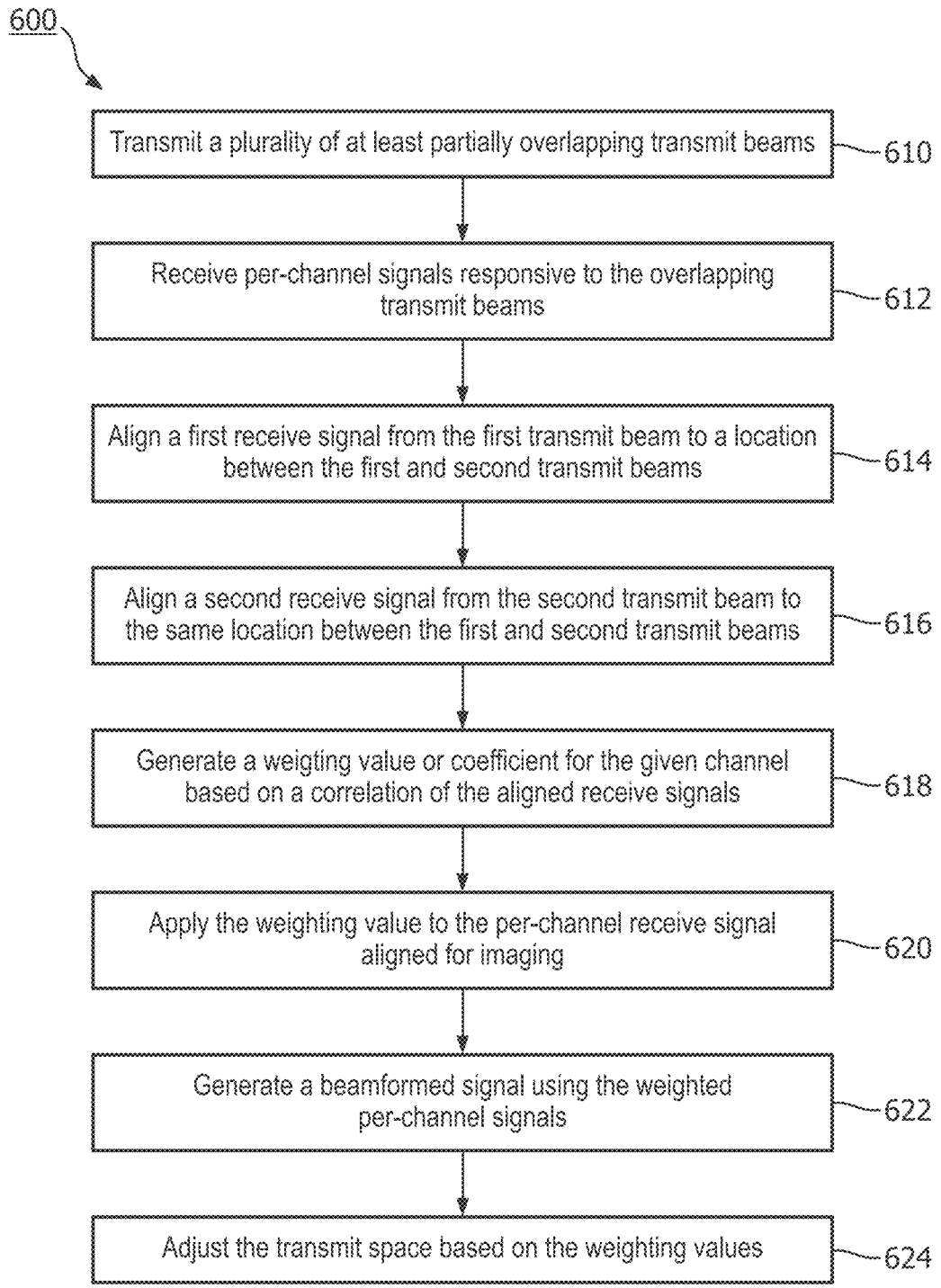
FIG. 6 shows a flow diagram of a process for ultrasound imaging in accordance with some examples herein.

FIG. 6 shows a flow diagram of a process 600 of ultrasound imaging in accordance with principles of the present disclosure. As shown in FIG. 6, the process involves, as shown in block 610, transmitting a plurality of at least partially overlapping transmit beams (e.g., a first transmit beam and a second transmit beam). As previously described, the first and second transmit beams may overlap at least partially (e.g., as shown in FIG. 2A) and may be interchangeably referred to as neighboring transmit beams or neighboring transmits. The overlapping or neighboring transmit beams may be transmitted from at least some of the elements of the array, namely elements associated with the active aperture during a given transmit-receive (or pulse-echo) cycle. During the receive event, echo signals responsive to a respective one of the neighboring transmits are detected by the elements and coupled to the beamformer via respective channels. As described, individual channels may couple signals from individual elements of the array or partially beamformed signals associated with a patch or sub-grouping of elements of the active aperture. As shown in block 612, the method further includes receiving the per-channel signals detected responsive to the neighboring transmits, and specifically in this example receiving a first receive signal responsive to the first transmit beam and a second receive signal responsive to the second transmit beam.

The received signals at a given channel may be appropriately time or phase-aligned (e.g., for coherent summing and subsequent image line generation) in accordance with any suitable transmit-receive sequence, such as retrospective and/or multiline beamforming sequence. For the purposes of noise clutter suppression, the first and second receive signals are aligned to the same common location between the first and second transmit beams, thus resulting in a set of two aligned signals, as shown in blocks 614 and 616. A coherence metric (e.g., based on a correlation between the set of aligned signals for the given channel, as shown in block 618) may be computed and used for masking the receive signal and/or for altering the transmit space. As previously describe, high correlation may indicate no blockage of the given channel and thus a higher gain may be used for the signal at the given channel. Conversely, low correlation may indicate blockage at that channel and thus a lower gain may be applied to the per-channel signal at that channel. As described herein, the location to which the signals are aligned for purposes of clutter suppression may be the same as used for imaging or it may be different in which case additional delay lines may be provided for generating the additional aligned signals.

As further shown in block 620, the method may proceeds by applying the weighting value to the per-channel receive signal, and then, at block 622, summing the weighted per-channel signals to generate a beamformed signal for image generation. In some embodiments, the blockage determination may also be used to adaptively adjust subsequent transmits. For example, as shown in block 624, the transmit space may be altered by adjusting the power to certain elements (e.g., reducing power output to blocked elements of the array).

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure, it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods. Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
   an array of transducer elements;
   a controller coupled to the array and configured to control the array to transmit a plurality of adjacent transmit beams toward a medium, the plurality of adjacent transmit beams comprising a first transmit beam and a second transmit beam at least partially overlapping the first transmit beam, wherein the first transmit beam is transmitted along a first transmit path and the second transmit beam is transmitted along a second transmit path; and
   a beamformer coupled to the array via a plurality of channels and configured to receive, at a given channel, a first receive signal and a second receive signal responsive to the first transmit beam and the second transmit beam, respectively, wherein the beamformer is further configured to:
      align the first receive signal to a physical location along a receive line, the receive line being located between the first and second transmit paths, to produce a first aligned receive signal;
      align the second receive signal to the physical location along the receive line between the first and second transmit paths to produce a second aligned receive signal;
      generate a weighting value for the given channel based on a correlation of the first and second aligned receive signals;
      apply the weighting value to at least one of the first and second aligned receive signals, to a receive signal aligned to a location other than the physical location between the first and second transmit paths, or a combination thereof, to produce a weighted per-channel signal for the given channel; and sum the weighted per-channel signals associated with multiple channels of the beamformer to produce a beamformed signal for ultrasonically imaging the medium.

2. The ultrasound imaging system of claim 1, wherein the beamformer is configured to generate the weighting value based on correlating the first and second aligned receive signals at multiple depth locations in the medium.

3. The ultrasound imaging system of claim 1, wherein the beamformer is configured to compare the correlations of the aligned receive signals from multiple sets of aligned receive signals and wherein the weighting value is based on the comparison such that when the correlations of the aligned receive signals are high, a higher weighting value is applied and when the correlations of the aligned receive signals are low, a lower weighting value is applied, wherein the correlations are determined to be high or low based on a statistical measure.

4. The ultrasound imaging system of claim 1, wherein the beamformer is configured to compute a normalized cross-correlation value and use the normalized cross-coefficient value as the weighting value.

5. The ultrasound imaging system of claim 1, wherein the beamformer is further configured to bandpass filter the aligned receive signals before computing the weighting value.

6. The ultrasound imaging system of claim 1, wherein the beamformer is configured to compute a cross-correlation value using a kernel spanning 3 to 5 wavelengths in fast time or 1 to 3 scan lines in beam space.

7. The ultrasound imaging system of claim 1, wherein an amount of overlap of the plurality of at least partially overlapping transmit beams is selected to achieve a beam density from 80 to 128 transmit events in a 90 degree span.

8. The ultrasound imaging system of claim 1, wherein the beamformer is configured to simultaneously receive multiple receive signals from the array via multiple channels from the plurality of channels of the active aperture and perform multiline receive beamforming in real-time using the multiple received signals.

9. The ultrasound imaging system of claim 1, wherein the controller is configured to adjust power output to one or more elements of the array based on the correlation of the aligned receive signals.

10. A method of ultrasonically imaging a medium, the method comprising:
transmitting, from an array of transducer elements, a plurality of at least partially overlapping transmit beams including a first transmit beam and a second transmit beam, wherein the first transmit beam is transmitted along a first transmit path and the second transmit beam is transmitted along a second transmit path;
receiving, at a given channel associated with the active aperture of the array, a first receive signal responsive to the first transmit beam and a second receive signal responsive to the second transmit beam;
aligning the first receive signal to a physical location along a receive line, the receive line being located between the first and second transmit paths, to produce a first aligned receive signal;
aligning the second receive signal to the physical location along the receive line between the first and second transmit paths to produce a second aligned receive signal;
generating a weighting value for the given channel based on a correlation of the first and second aligned receive signals;
applying the weighting value to at least one of the first and second aligned receive signals, to a receive signal aligned to a location other than the physical location between the first and second transmit paths, or a combination thereof, to produce a weighted per-channel signal for the given channel; and
summing the weighted per-channel signals associated with multiple channels of the active aperture to produce a beamformed signal for ultrasonically imaging the medium.

11. The method of claim 10, wherein the generating the weighting value comprises correlating the first and second aligned receive signals at multiple depth locations in the medium.

12. The method of claim 10, further comprising comparing the correlations of the aligned receive signals from multiple sets of aligned receive signals, wherein the weighting value is based on the comparison such that when the correlations of the aligned receive signals are high, a higher weighting value is applied and when the correlations of the aligned receive signals are low, a lower weighting value is applied, wherein the correlations are determined to be high or low based on a statistical measure.

13. The method of claim 10, wherein generating the weighting value comprises computing a normalized cross-correlation value and using the normalized cross-coefficient value as the weighting value.

14. The method of claim 10, further comprising bandpass filtering the aligned receive signals before computing the weighting value.

15. The method of claim 10, wherein the generating the weighting value comprises computing a cross-correlation value using a kernel spanning 3 to 5 wavelengths in fast time or 1 to 3 scan lines in beam space.

16. The method of claim 10, wherein the transmitting comprises transmitting the plurality of at least partially overlapping transmit beams such that they overlap by an amount selected to achieve a beam density from 80 to 128 transmit events in a 90 degree span.

17. The method of claim 10, wherein the plurality of at least partially overlapping transmit beams further includes a third transmit beam that overlaps at least partially with at least one of the first and second transmit beams, and wherein the weighting value is computed based on receive signals from the first, second, and third transmit beams aligned to a location between the first, second, and third transmit beams.

18. The method of claim 10, wherein the receiving comprises simultaneously receiving multiple receive signals from the array via multiple channels from the plurality of channels associated with the active aperture and performing multiline receive beamforming in real-time based on the multiple received signals.

19. The method of claim 10, further comprising adjust power output to one or more elements of the array based on the correlation of the aligned receive signals.

20. A non-transitory computer-readable medium comprising executable instructions, which when executed cause a processor of a medical imaging system to perform the method of claim 10.

* * * * *